(12) United States Patent
Wu et al.

(10) Patent No.: US 7,368,133 B2
(45) Date of Patent: May 6, 2008

(54) MEDICINAL DRUG AND METHODS OF MANUFACTURING THE SAME

(76) Inventors: Yu Ching Wu, 22605 Wood Shadow La., Lake Forest, CA (US) 92630; Mao Wu, #58, 361 Lane, Chungnan Rd., Pitou, Changhua (TW); Huo-Tu Wu, #1, Meiyuan Rd., Tsuluh, Taidong (TW)

( * ) Notice: Subject to any disclaimer, the term of this patent is extended or adjusted under 35 U.S.C. 154(b) by 0 days.

(21) Appl. No.: 11/286,752

(22) Filed: Nov. 25, 2005

(65) Prior Publication Data

US 2006/0105060 A1    May 18, 2006

Related U.S. Application Data

(63) Continuation-in-part of application No. 11/210,170, filed on Aug. 23, 2005, now abandoned.

(60) Provisional application No. 60/603,598, filed on Aug. 23, 2004.

(51) Int. Cl.
*A61K 36/00* (2006.01)
(52) U.S. Cl. .................................... 424/725
(58) Field of Classification Search ............ None
See application file for complete search history.

(56) References Cited

U.S. PATENT DOCUMENTS

| | | | |
|---|---|---|---|
| 5,773,004 | A | 6/1998 | Takahashi |
| 5,916,564 | A | 6/1999 | Lipsky et al. |
| 6,596,761 | B2 | 7/2003 | Lanzendorfer et al. |
| 6,753,325 | B2 | 6/2004 | Rosenbloom |
| 6,902,748 | B1 | 6/2005 | Lee et al. |
| 2003/0099725 | A1 | 5/2003 | Tze et al. |
| 2004/0014782 | A1 | 1/2004 | Krause |
| 2004/0028643 | A1 | 2/2004 | Chiba et al. |
| 2004/0156920 | A1 | 8/2004 | Kane |
| 2005/0159483 | A1 | 7/2005 | Bassaganya-Riera |

FOREIGN PATENT DOCUMENTS

| | | |
|---|---|---|
| JP | 02002179581 | 6/2002 |
| JP | 02004137166 | 5/2004 |

OTHER PUBLICATIONS

Naples, M.L. Weeds of Rain Fed Lowland Rice Fields of Laos & Cambodia. MSc thesis, University of Leiden (2005) www.nationalherbarium.nl/Riceweedsweb/www/ludwig.htm accessed Nov. 19, 2005.

*Primary Examiner*—Susan Coe Hoffman
(74) *Attorney, Agent, or Firm*—Roland Tong

(57) ABSTRACT

The present invention includes a medicinal drug comprising an *Axonopus* extract and *Ludwigia* extract dissolved in a pharmacologically acceptable solvent. The extract is able to reduce the production of pro-inflammatory cytokines and the proliferation of lymphocytes. The present invention also includes a method of treating inflammation with the extract.

15 Claims, No Drawings

MEDICINAL DRUG AND METHODS OF MANUFACTURING THE SAME

CROSS REFERENCE TO RELATED APPLICATIONS

This is a continuation-in-part application of currently application Ser. No. 11/210,170 filed on Aug. 23, 2005 now abandoned. This application claims priority to and incorporates by reference provisional application Ser. No. 60/603,598 filed on Aug. 23, 2004.

FIELD OF INVENTION

The present invention relates to drugs and body treating compositions.

BACKGROUND

Four Latin words—calor (heat), dolor (pain), rubor (redness), and tumor (swelling)—are conventionally used to describe the signs of inflammation. Inflammation is conventionally managed by using over the counter remedies, such as ibuprofen. Some herbal medicines are used to manage inflammation. For instance, in Malaysia, China, and Indo-China, aerial parts of *Ludwigia* are used to manage inflammatory skin diseases, like boils, ulcers, and impetigo (Naples, M. L. (2205). Weeds of Rain Fed Lowland Rice Fields of Laos & Cambodia. Unpublished MSc thesis, University of Leiden *Ludwigia octovalvis* and *Ludwigia hyssopifolia* reportedly have been used as anti-inflammatories in maintaining skin (Japanese patent publication JP02002179581).

*Ludwigia* belongs to the family of Onagraceae and can be found in Taiwan, Japan, China and India. The medicinal usage of this genus can be found in several Chinese medicinal books to also treat cuts, chronic nephritis or hydronephrosis, and toothache. The present inventor has explored further the previously known ways of using *Ludwigia* as a therapeutic plant. For instance, in the present inventor's exploration, the present inventor found pharmacologically proper formulations that render therapeutic effects, including anti-inflammatory effects. The present inventor also found that pharmacologically proper formulations of extracts containing *Ludwigia* may be used to treat burn injuries. The present inventor has further found that smaller and pharmacologically proper formulations of *Ludwigia* reduce production of pro-inflammatory cytokines and the proliferation of peripheral blood mononuclear cells. Finally, the present inventor has found other ingredients that may be used with *Ludwigia* to treat inflammation.

BRIEF DESCRIPTION

The present invention includes a medicinal drug comprising an *Axonopus* extract and
*Ludwigia* extract dissolved in a pharmacologically acceptable solvent. The present invention also includes a method of treating inflammation. The method includes administering to a subject an extract of *Axonopus* and *Ludwigia*, which is preferably dissolved in a pharmacologically acceptable solvent. The extract is able to reduce production of pro-inflammatory cytokines.

The above description sets forth, rather broadly, a summary of certain embodiments of the present invention so that the detailed description that follows may be better understood and contributions of the present invention to the art may be better appreciated. Some of the embodiments of the present invention may not include all of the features or characteristics listed in the above summary. There are, of course, additional features of the invention that will be described below and will form the subject matter of claims. In this respect, before explaining at least one preferred embodiment of the invention in detail, it is to be understood that the invention is not limited in its application to the details of the construction and to the arrangement of the components set forth in the following description or as illustrated in the drawings. The invention is capable of other embodiments and of being practiced and carried out in various ways. Also, it is to be understood that the phraseology and terminology employed herein are for the purpose of description and should not be regarded as limiting.

DETAILED DESCRIPTION

The present invention comprises various embodiments of a medicinal drug and various methods of manufacturing the medicinal drug. In vitro and in vivo studies with the medicinal drug show anti-inflammatory effects, and thus the medicinal drug may be used to treat injuries that involve inflammation, such as second to third degree burn injuries. The anti-inflammatory benefits may include the reduction of symptoms due to inflammation, such as pain, swelling, redness, and itchiness.

In the preferred embodiment, the medicinal drug is prepared by using the leaves of *Axonopus* and *Ludwigia*. The percentage of *Axonopus* relative to *Ludwigia* is preferably in the range of 0-75% *Axonopus* and 25-100% *Ludwigia*. *Axonopus* may be either *Axonopus affinis* or *Axonopus compresses* (Sw.) P.Beauv.var.affinis. *Axonopus* belongs to the family of Gramineae and grows in warm and humid climate, such as South America, Southeast Asia, and Taiwan. In the in vitro and in vivo studies described below, equal amounts of *Axonopus* and *Ludwigia* leaves, which were harvested from Taiwan, were used. *Ludwigia* may either be *Ludwigia octovalvis, Ludwigia prostrate, Ludwigia hyssopifolia, Ludwigia epiloboides, Ludwigia ovalis, Ludwigia adscendens, Ludwigia peploides*, and *Ludwigia perennis*.

The leaves are preferably blended with water using a mechanical blender. The blended leaves are preferably poured into a nylon filter and rinsed with water until the green color of chlorophyll disappears from the blended leaves. The blended leaves are preferably air dried and ground to powder. 16 grams of blended leaves typically result in 1 gram of powder when the powder making steps above are followed. Next, a total of 0.1-3.00 gram of *Axonopus* and *Ludwigia* powder is preferably soaked in 100 ml. of distilled deionized water or 10% ethanol for 3-7 days at room temperature. Other known pharmacologically acceptable solvents may be used. The mixture is preferably filtered through a 0.22 or a 1 micrometer filter paper to produce the extract.

In an alternative method, the medicinal drug of the present invention may be fractionated and be made with a molecular weight (m.w.) of not more than 5,000 by size exclusion chromatography, which is a technique known in the art. 0.25-2.00 g. of powder containing *Ludwigia* and *Axonopus* may be weighed and soaked in 7 ml. of 15-20% ethanol for 2-7 days. The powder mixture is preferably filtered through a 1 micrometer filter paper. The filtrate is preferably loaded into a size exclusion column, which may be a C16/100 column with Sephadex G-25C gel (Amersham Scientific, Piscataway, N.J.). Void volume that would include compounds greater than 5,000 in molecular weight is preferably eluted out. Void volume is preferably measured by bovine hemoglobin, and molecular weight is preferably referenced by phenol red. After said void volume is eluted out, an extract having less than 5,000 m.w. may be collected. 100 ml. of said extract is preferably collected and mixed with 0.6 gram of carbomer and 0.5-1 ml. of sodium hydroxide to form an extract gel.

In Vitro Studies

In the preferred embodiment, the anti-inflammatory effect of the medicinal drug of the present invention was studied by monitoring the amount of interleukin 2 and tumor necrosis factor in a cell culture. Interleukin 2 (IL2), also known as T-cell growth factor, is a lymphokine that is released by helper T cells in response to an antigen and interleukin-1. IL2 stimulates the proliferation of effector lymphocytes, including helper T cells, cytotoxicity T cells, and NK cells to mediate the removal of pathogens from body without the need for further differentiation. (Hunter, C. A., and Reiner, S. L.: Cytokines and T cells in host defense. Curr. Opin. Immunol. 2000, 12:413-418.) The cytokine release and the cascade of reactions during the process of removal of pathogens at least partially causes inflammation. Thus, anti-inflammatory effect may be realized when there is a reduction of IL2 that is being released.

Anti-inflammatory effect may also be realized when there is a reduction of TNF alpha. Tumor necrosis factor (TNF) alpha is a pro-inflammatory cytokine that is produced by white blood cells (macrophages, NK cells, and T cells). TNF alpha is a polypeptide of molecular weight 17500 and whose primary and tertiary structure has been elucidated (Pennisca, D. et al. Nature 312:724 (1984) and Jones, E. Y. et al. Nature 338: 225 (1989)). After infection, TNF alpha is released by macrophages, NK cells, and T cells to mediate the removal of pathogens and ceases the symptoms of inflammation. Thus, TNF alpha is considered as a mediator of inflammation. (See, generally, Beutler, B. and Cerami, A., Nature 320: 584 (1986).

Human peripheral blood mononuclear cells (PBMC) were isolated from whole blood using Ficoll-Paque Plus (Amersham Scientific, Piscataway, N.J.). Isolated PBMC were then plated in 24 well plates using RPMI with 10% fetal calf serum (FCS). In each well, $5 \times 10^6$ of PBMC was used per ml. Each well plate had a total volume of 1 ml. The well plates were incubated at 37 C and 5% $CO_2$ for 2 hours. Next, the cells were rinsed off with culture media. The non-adherent peripheral blood leukocytes (NA-PBLs), which include mainly lymphocytes, were recounted. 100 microliters of NA-PBLs were then plated in 96-well plates using $1 \times 10^6$ per ml. of culture media, which is preferably RPMI and 10% FCS.

Phytohemagglutinin (PHA) is a mitogen, which stimulates the cells to produce pro-inflammatory cytokines. Some of the well plates were treated with 1:100 PHA solution. Some were left untreated. 5 microliter of the diluted extract (1:150) was added to some of the well plates to compare the effect of the extract on the cells. Supernatants from the well plates were collected at 48 and 72 hours for TNF alpha and IL-2 measurement by ELISA. The NA-PBLs were stained with MTT after 72 hours of incubation to measure the cell proliferation.

The remaining cells (mainly monocytes) that adhere to the well were trypsonized off the well, incubated with cold phosphate-buffered saline (PBS) in refrigerator for 30 minutes, scraped off from the well using a rubber policeman, recounted, and washed with RPMI. The remaining cells were then plated in 96-well plate at $2 \times 10^5$ per ml. RPMI1640 complete media with 10% FCS. Half of the well plates were treated with 1:100 PHA solution per well. The other half were left untreated. 5 microliter of the diluted extract (1:150) was added to some of the well plates to compare the effect of the extract on the cells. Supernatants from the well plates were collected at 48 and 72 hours fro TNF-alpha and IL-2 measurement by ELISA.

Tables 1-4 below are the results of the in vitro studies. The abbreviation A/L means the extract of *Axonopus compresses* and *Ludwigia octovalis*.

TABLE 1

IL-2 Production After 48 Hours of Incubation (pg/ml)

| | NA-PBL | monocytes |
|---|---|---|
| Control | −32.2 | −38.6 |
| A/L | −31.7 | −36.6 |
| PHA | 1345 | 626 |
| PHA + A/L | 858 | 333.2 |

TABLE 2

TNF Alpha Production After 48 Hours of Incubation (pg/ml)

| | NA-PBL | monocytes |
|---|---|---|
| Control | −22.1 | −16.2 |
| A/L | 5.1 | 15.7 |
| PHA | 435.8 | 321.4 |
| PHA + A/L | 341.8 | 280.1 |

TABLE 3

TNF Alpha Production After 72 Hours of Incubation (pg/ml)

| | NA-PBL | monocytes |
|---|---|---|
| Control | −18.1 | −19.7 |
| A/L | 6.3 | 20.4 |
| PHA | 276.55 | 304.8 |
| PHA + A/L | 191.3 | 242.3 |

TABLE 4

NA-PBL Proliferation Assay Read at OD490 and OD570

| | OD490 | OD570 |
|---|---|---|
| Control | 0.105 | 0.162 |
| A/L | 0.107 | 0.163 |
| PHA | 0.256 | 0.488 |
| PHA + A/L | 0.205 | 0.399 |

It can be appreciated that the extract reduces the production of IL-2 by approximately 30% for the non-adherent PBL and approximately 48% for the monocytes after 48 hours of incubation. The extract reduces the production of TNF-alpha by approximately 15% for the non-adherent PBL and 15% for the monocytes after 48 hours of incubation. The extract further reduces TNF alpha production by approximately 35% for the non-adherent PBL and 20% for the monocytes after 72 hours of incubation. The proliferation assay shows approximately 25% inhibition with the presence of the extract.

In Vivo Studies 100 ml of the extract was mixed with 0.6 gram of carbomer and 0.5-1 ml. of sodium hydroxide to form an extract gel. A placebo gel was prepared with the same ingredients but without the extract. Wild type mice were anesthetized with ether and their thighs were shaved. Second to third degree burn and inflammation were induced on the mice by applying cotton, which was soaked in boiling water, on the shaved area for 15 seconds. Two minutes after the burn was induced on each mouse, either the extract gel or the placebo gel was applied on the burn area. Extract gel or placebo gel was re-applied on the burn area approximately 6 hours after the first application. The treatments were re-administered twice a day thereafter.

In a second set of in vivo studies, all the steps above were repeated except with the use of 100 ml. of fractionated extract from the size exclusion chromatography described above. The following results were obtained from two in vivo studies.

TABLE 5

First In Vivo Study

| Treatments | No. of mice tested | Duration from burn to complete heal | |
|---|---|---|---|
| | | Mean (days) | S.D. |
| Placebo | 7 | 29.4 | 12.4 |
| 0.1% A/L extract | 6 | 20.3 | 3.2 |
| 0.5% A/L extract | 7 | 13.3 | 2.4 |

S.D.: Standard deviation

TABLE 6

Second In Vivo Study

| Treatments | No. of mice tested | Duration from burn to complete heal | |
|---|---|---|---|
| | | Mean (days) | S.D. |
| Placebo | 4 | 21.8 | 3.0 |
| A/L whole extract | 4 | 16.0 | 2.2 |
| A/L extract (less than 5,000 m.w.) | 5 | 14.2 | 1.3 |

The term complete heal means that redness and swelling can no longer be seen from the treated mice, and the burned skin has been replaced with new skin. It can be realized that the present invention provides an anti-inflammatory agent that can expedite the healing of a burn by approximately 9-16 days. Thus, it can be appreciated that the present invention provides an effective anti-inflammatory agent, as it has shown to reduce the symptoms of inflammation, such as swelling and redness. The present invention provides a drug that may be used to treat second to third degree burn injuries and other inflammation-related problems.

Although the description above contains many specifications, these should not be construed as limiting the scope of the invention but as merely providing illustrations of some of presently preferred embodiments of this invention. For instance, the medicinal drug may be made in liquid, powder, gel, capsule, tablet, or granular form. Additional herbs known in the art may be used with the extract to improve the shelf life or the efficacy of the drug delivery. The order in which the steps are presented above is not limited to any particular order and does not necessarily imply that they have to be performed in the order presented. It will be understood by those of ordinary skill in the art that the order of these steps can be rearranged and performed in any suitable manner. It will further be understood by those of ordinary skill in the art that some steps may be omitted or added and still fall within the spirit of the invention. Thus the scope of the invention should be determined by the appended claims and their legal equivalents rather than by the examples given.

The invention claimed is:

1. A medicinal drug comprising:
   a. water or ethanol *Axonopus* extract; and
   b. water or ethanol *Ludwigia* extract.

2. The medicinal drug of claim 1, wherein the medicinal drug is effective in reducing the production of pro-inflammatory cytokines.

3. The medicinal drug of claim 2, wherein the cytokine is a TNF alpha.

4. The medicinal drug of claim 2, wherein the cytokine is an interleukin 2.

5. The medicinal drug of claim 1, wherein said *Axonopus* extract is from an *Axonopus* plant, said *Axonopus* plant being selected from the group consisting of *Axonopus affinis* and *Axonopus compressus*.

6. The medicinal drug of claim 1, wherein the medicinal drug is able to reduce the proliferation of peripheral blood mononuclear cells.

7. The medicinal drug of claim 1, wherein the medicinal drug is used to treat inflammation.

8. The medicinal drug of claim 1, further comprising carbomer and sodium hydroxide mixed with the *Ludwigia* and *Axonopus* extract forming a gel.

9. A method of manufacturing a medicinal drug, the method comprising dissolving *Axonopus* and *Ludwigia* in a water or ethanol to create an extract, wherein the extract may be administered to a subject to treat inflammation.

10. The method of claim 9, the extract being able to reduce production of pro-inflammatory cytokines.

11. The method of claim 10, wherein the cytokine is a TNF alpha.

12. The method of claim 10, wherein the cytokine is an interleukin 2.

13. The method of claim 9, wherein the extract is able to reduce the proliferation of peripheral blood mononuclear cells.

14. The method of claim 9, wherein the extract reduces redness from the inflammation.

15. The method of claim 9, wherein the inflammation comes from a burn injury.

* * * * *